US00PP09596P

United States Patent [19]

Trees

[11] Patent Number: Plant 9,596

[45] Date of Patent: Jun. 25, 1996

[54] GERANIUM PLANT NAMED BFP-790 PINK PARFAIT

[75] Inventor: Scott C. Trees, Arroyo Grande, Calif.

[73] Assignee: Geo. J. Ball, Inc., West Chicago, Ill.

[21] Appl. No.: 422,693

[22] Filed: Apr. 14, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 8,962 10/1994 Klemm ..... Plt./87.12

*Primary Examiner*—James R. Feyrer

*Attorney, Agent, or Firm*—Burns, Doane, Swecker & Mathis

[57] ABSTRACT

A new and distinct *Pelargonium×hortorum* cultivar named 'BFP-790 Pink Parfait' is provided. This new Zonal Geranium cultivar was the result of a controlled breeding program wherein a plant designated 1797-1 (non-patented in the United States) was pollinated by the plant designated 2006-2 (non-patented in the United States). The new cultivar forms attractive semi-double tricolored florets with medium pink petals having a distinct large rose pink freckle and a white eye on each petal. Attractive dark green foliage is well retained during shipment. The growth habit is medium self-branching and does not require the use of a growth regulator.

1 Drawing Sheet

SUMMARY OF THE INVENTION

The present invention comprises a new and distinct Geranium cultivar, botanically known as *Pelargonium×hortorum* Bailey, and hereinafter is referred to by the cultivar name 'BFP-790 Pink Parfait'.

The new cultivar is a product of a planned breeding program which had the objective of the creation of a new Geranium cultivar that exhibits uniform flowers, dark green foliage, a medium self-branching growth habit that requires no growth regulator, a propensity for rapid rooting, and a stable foliage coloration during shipment.

The breeding program that resulted in the production of the new cultivar of the present invention was carried out in a controlled environment during 1992 at Arroyo Grande, Calif., U.S.A. The female patent (i.e., seed parent) was a plant designated 1797-1 (non-patented in the United States) which exhibits semi-double lavender florets with a white eye and medium green foliage. The male parent (i.e., pollen parent) was a plant designated 2006-2 (non-patented in the United States) which exhibits single light pink florets with dark green foliage. The parentage of the 'BFP-790 Pink Parfait' cultivar can be summarized as follows:

1797-1×2006-2.

'BFP-790 Pink Parfait' was discovered and selected during 1992 as a highly distinctive flowering plant from among the pogeny of the stated cross at Arroyo Grande, Calif., U.S.A. This plant was initially designated BFP-790.

It was found that the new cultivar of the present invention:

(a) exhibits attractive semi-double tricolored florets with medium pink petals having a large rose pink freckle and a white eye on each petal,
(b) forms attractive dark green foliage, and
(c) exhibits a medium self-branching growth habit in the absence of a growth regulator.

The florets are considered to be semi-double in that (1) the petals overlap to some degree, (2) they commonly exhibit 5 to 6 petals per floret, and (3) additionally they commonly possess 1 to 2 petaloids per floret. The white claw portion of the petals contains primary veins that are rose pink and generally match the freckles. Such veins contrast with the white claw portion. The vein definition is typically more distinct in the upper petals and less distinct in the lower petals.

When plant material of the 'BFP-790 Pink Parfait' cultivar is subjected to standard random amplified polymorphic DNA marker analysis (RAPD) using polymerase chain reaction (PCR) and a known set of DNA primers, it is found to exhibit a distinctive fingerprint map which is on file at the Ball FloraPlant Division of Geo. J. Ball, Inc. at Arroyo Grande, Calif., U.S.A.

The first act of asexual reproduction of the 'BFP-790 Pink Parfait' cultivar was accomplished when vegetative cuttings were taken from the initial selection in a controlled environment at Arroyo Grande, Calif., U.S.A., by a technician working under the direction and supervision of the originator of the new cultivar. Horticultural examination of plants resulting from such asexual propagation during 1993 has demonstrated that the combination of characteristics as herein described for the 'BFP-790 Pink Parfait' cultivar is firmly fixed and is retained through successive generations of such asexual reproduction.

The new 'BFP-790 Pink Parfait' cultivar has not been observed under all possible environmental conditions. Accordingly, the described phenotype may vary somewhat with variations in the environment, such as temperature, light intensity, and day length.

Of the many commercial cultivars, the 'Blues' cultivar (U.S. Plant Pat. No. 5,373) is considered to be the most similar to the new 'BFP-790 Pink Parfait' cultivar. When the new cultivar of the present invention is compared to the 'Blues' cultivar, it is found that the 'BFP-790 Pink Parfait' cultivar exhibits a less compact growth habit (e.g., approximately 25 to 31 cm. in height vs. approximately 22 to 25 cm.), smaller florets (e.g., approximately 4.2 to 4.5 cm. vs. approximately 4.9 to 5.1 cm.), and larger leaves (e.g., approximately 9.7 to 11.0 cm.×8.0 to 8.7 cm. vs. 7.0 to 8.5 cm.×6.0 to 7.0 cm.).

The new cultivar of the present invention is being marketed by Geo. J. Ball, Inc. under the Showcase trademark.

BRIEF DESCRIPTION OF THE PHOTOGRAPH

The accompanying photograph of FIG. 1 shows typical characteristics of the new 'BFP-790 Pink Parfait' cultivar with colors generally being as nearly true as it is reasonably possible to make the same in color illustrations of this character. Typical flower and foliage characteristics are illustrated. The plant was being grown in a greenhouse at West Chicago, Ill., U.S.A.

DETAILED DESCRIPTION

Figure 1:
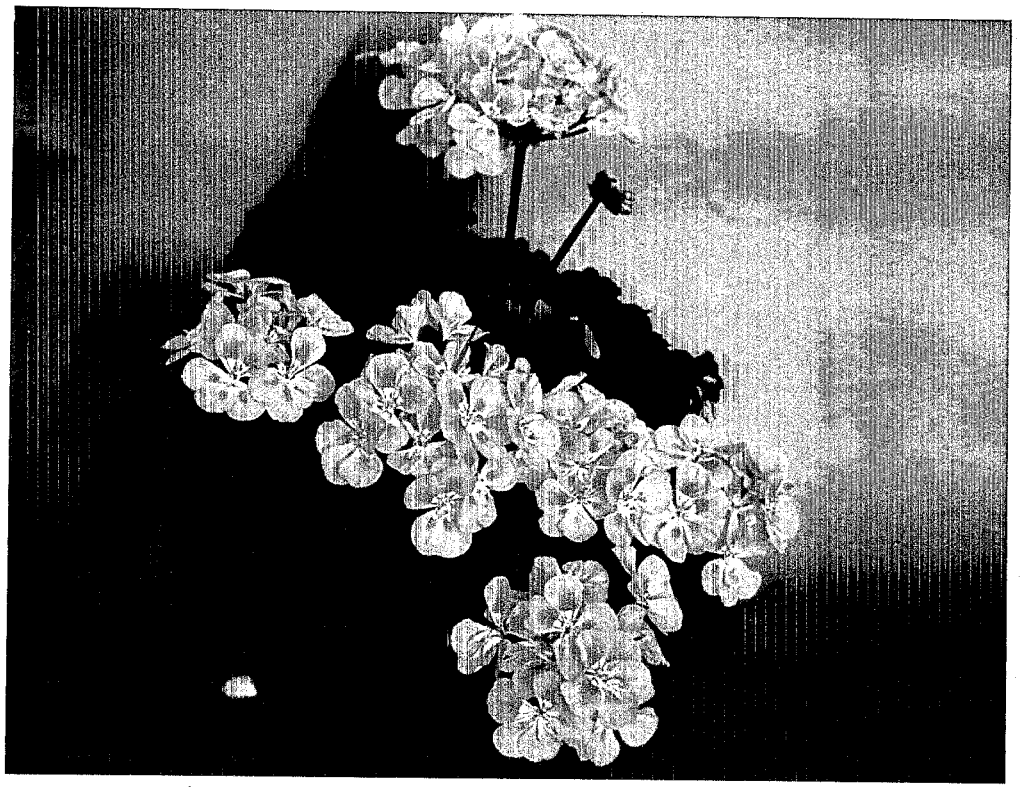

The following observations, measurements and comparisons describe plants grown in Ball FloraPlant's greenhouses at West Chicago, Ill., U.S.A. under greenhouse conditions which approximate those generally used in commercial practice. In the following description, color references are made to the R.H.S. Colour Chart of The Royal Horticultural Society, London, England. The color values were determined between 11:00 and 11:45 a.m. on Jan. 3, 1995, under natural light conditions of 2,000 footcandles.

Classification:

*Botanical.*—*Pelargonium×hortorum* Baily, cv. 'BFP-790 Pink Parfait'.

*Commercial.*—Zonal Geranium.

Inflorescence

A. Umbel:

*Average diameter.*—Approximately 10.5 to 12.5 cm. compared to approximately 10.0 to 11.0 cm. for the 'Blues' cultivar.

*Average depth.*—Approximately 6.5 to 7.5 cm. compared to approximately 6.0 to 8.5 cm. for the 'Blues' cultivar.

*Peduncle length.*—Approximately 15.5 to 20.0 cm. compared to approximately 14.0 to 18.0 cm. for the 'Blues' cultivar.

*Pedicel length.*—Approximately 3.5 to 4.2 cm. compared to approximately 3.0 to 3.7 cm. for the 'Blues' cultivar.

*Pedicel color.*—Yellow Green Group 146D.

*Number of umbels plant.*—When grown in a 10 cm. pot at 9 weeks after the sticking of a rooted cutting, there commonly are 2 to 3 umbels per plant. This compares to approximately 3 to 4 umbels per plant for the 'Blues' cultivar.

*Number of florets umbel.*—When grown in a 10 cm. pot at 9 weeks after the sticking of a rooted cutting, there commonly are approximately 32 to 35 florets per umbel. This compares to approximately 28 to 35 florets per umbel for the 'Blues' cultivar.

B. Corolla:

*Average diameter.*—Approximately 4.2 to 4.5 cm. compared to approximately 4.9 to 5.1 cm. for the 'Blues' cultivar.

*Form.*—Both the 'BFP-790 Pink Parfait' cultivar and the 'Blues' cultivar are semi-double with petaloids.

*Number of petaloids.*—Commonly approximately 1 to 2 petaloids per floret are present. This compares to approximately 1 petaloid for the 'Blues' cultivar.

*Color.*—General tonality from a distance of three meters: Bright pink with large rose pink freckle an white center on each petal. Adaxial: Background color is Red-Purple Group 73A with white attachment points and dark rose freckle of Red-Purple Group 57A at the center of each petal. This compares to Red-Purple Group 68B with a freckle of Red Group 52A for the 'Blues' cultivar. Abaxial: Red-Purple Group 73C. This compares to Red-Purple Group 68D for the 'Blues' cultivar.

C. Bud:

*Shape.*—Oval-rounded.

*Color — Adaxial.*—Red-Purple Group 73B compared to Red-Purple Group 68C for the 'Blues' cultivar.

*Color — Abaxial.*—Red-Purple Group 73D compared to Red-Purple Group 68D for the 'Blues' cultivar.

D. Reproductive organs:

*Androecium.*—The anthers are commonly approximately 2 mm. in length. The pollen color for both the 'BFP-790 Pink Parfait' cultivar and the 'Blues' cultivar is Orange-Red Group 31A. The filaments commonly number approximately 8, and are approximately 4 to 7 mm. in length. The anthers present on each filament commonly measure approximately 2 mm. in length.

*Gynoecium.*—The pistil length commonly is approximately 5 mm. There is a single stigma which commonly has a length of approximately 4 mm. which commonly branches into 5 parts, and the style length commonly is approximately 5 mm.

*Fertility.*—Usually does not produce fruits in the absence of mechanical fertilization.

E. Spring flowering response period: Approximately 6 to 7 weeks from rooted cuttings under standard greenhouse conditions.

F. Outdoor flower production: Freely flowering under outdoor growing conditions with substantially continuous blooming.

G. Durability: Ships well.

Plant

A. Foliage: Dark green without zonation.

*Form.*—Reniform, with cordate base.

*Margin.*—Crenate.

*Color.*—Adaxial: Slightly darker than Green Group 137A for both the 'BFP-790 Pink Parfait' cultivar and the 'Blues' cultivar. Abaxial: Green Group 137C for the 'BFP-790 Pink Parfait' cultivar and Green Group 136A for the 'Blues' cultivar.

*Size.*—Approximately 9.7 to 11.0 cm. at the widest point and approximately 8.0 to 8.7 cm. at the narrowest point. This compares to approximately 7.0 to 8.5 cm. at the widest point and approximately 6.0 to 7.0 cm. at the narrowest point for the 'Blues' cultivar.

*Leaf petioles.*—Commonly approximately 6 to 9 cm. in length.

B. General appearance and form:

*Internode length.*—Commonly varies from approximately 1.3 to 2.3 cm. This compares to approximately 1.5 to 3.0 cm. for the 'Blues' cultivar.

*Branching pattern.*—Freely basal branching. No pinching is required to obtain self-branching. A medium self-branching growth habit is exhibited in the absence of the use of a growth regulator.

*Height.*—Approximately 25 to 31 cm. above a 10 cm. pot at 9 weeks under standard greenhouse conditions. This compares to approximately 22 to 25 cm. for the 'Blues' cultivar.

I claim:

1. A new and distinct Geranium plant named 'BFP-790 Pink Parfait', substantially as herein shown and described, which:

(a) exhibits attractive semi-double tricolored florets with medium pink petals having a large rose pink freckle and a white eye on each petal, (b) forms attractive dark green foliage, and (c) exhibits a medium self-branching growth habit in the absence of a growth regulator.

* * * * *